(12) United States Patent
Leitner et al.

(10) Patent No.: US 7,482,501 B2
(45) Date of Patent: Jan. 27, 2009

(54) PROCESS FOR CONTINUOUS RINGCLOSING METATHESIS IN COMPRESSED CARBONDIOXIDE

(75) Inventors: Walter Leitner, Aachen (DE); Nils Theyssen, Dortmund (DE); Zhenshan Hou, Muelheim an der Ruhr (DE); Konstantin Walter Kottsieper, Wuppertal (DE); Maurizio Solinas, Sassari (IT); Daniela Giunta, Sassari (IT)

(73) Assignees: Boehringer Ingelheim International GmbH, Ingelheim (DE); Studiengesellschaft Kohle mbH, Muelheim an der Ruhr ( * ) Notice: Subject to any disclaimer, the term of this patent is extended or adjusted under 35 U.S.C. 154(b) by 0 days.

(21) Appl. No.: 11/275,564

(22) Filed: Jan. 17, 2006

(65) Prior Publication Data
US 2006/0252951 A1    Nov. 9, 2006

(30) Foreign Application Priority Data
Jan. 17, 2005    (DE) .................. 10 2005 002 336

(51) Int. Cl.
*C07C 5/00*    (2006.01)
*C07F 15/00*    (2006.01)
*B01J 31/00*    (2006.01)

(52) U.S. Cl. .................. 585/353; 556/136; 585/520
(58) Field of Classification Search ................ 556/136; 585/353, 520
See application file for complete search history.

(56) References Cited

U.S. PATENT DOCUMENTS

| | | | |
|---|---|---|---|
| 5,840,820 A * | 11/1998 | DeSimone et al. | 528/34 |
| 6,348,551 B1 * | 2/2002 | Furstner et al. | 526/171 |
| 6,608,027 B1 | 8/2003 | Tsantrizos et al. | |
| 6,756,500 B1 | 6/2004 | Guertler et al. | |
| 7,119,072 B2 | 10/2006 | Llinas-Brunet et al. | |
| 7,148,347 B2 | 12/2006 | Brandenburg et al. | |
| 7,189,844 B2 | 3/2007 | Gallou et al. | |
| 7,268,211 B2 | 9/2007 | Gallou et al. | |
| 2003/0181363 A1 | 9/2003 | Llinase-Brunet et al. | |
| 2004/0248779 A1 | 12/2004 | Dersch et al. | |
| 2005/0075279 A1 | 4/2005 | Llinas-Brunet et al. | |
| 2005/0080005 A1 | 4/2005 | Llinas-Brunet et al. | |

FOREIGN PATENT DOCUMENTS

| | | |
|---|---|---|
| WO | 0059929 A1 | 10/2000 |
| WO | 0202218 A1 | 1/2002 |
| WO | 03064455 A2 | 8/2003 |
| WO | 2005028501 A1 | 3/2005 |
| WO | 2005056185 A1 | 6/2005 |
| WO | 2005090383 A2 | 9/2005 |

OTHER PUBLICATIONS

Fürstner et al., Angew. Chem. Int. Ed. Engl., vol. 36, No. 22, pp. 2466-2469 (1997).*
Sellin, et al; Continuous flow homogeneous catalysis: htdroformylationof alkenes in supercritical fluid-ionic liquid biphasic mixtures; Chemical Communications; Chemcom, Royal Society of Chemistry; GB; 2001; pp. 781-782.
Brown, et al; Asymmetric Hydrogenation and Catalyst Recycling Using Ionic Liquid and Supercritical Carbon Dioxide; Journal of the American Chemical Socity; Washington, DC; vol. 123, No. 6; Jan. 17, 2001; pp. 1254-1255.
Gordon; New Developments in catalysis using liquids; Applied Catalysis A: General, Elsevier Science; Amsterdam, NL; vol. 222; No. 1-2; Dec. 20, 2001; pp. 101-117.
International Search Report for corresponding PCT/EP2006/050195.
Fuerstner et al.; Olefin Metathesis in Supercritical Carbon Dioxide; Journal of the American Chemical Society; 2001; vol. 123: pp. 9000-9006.

* cited by examiner

*Primary Examiner*—Porfirio Nazario-Gonzalez
(74) *Attorney, Agent, or Firm*—Michael P. Morris; Mary-Ellen M. Devlin; Philip I. Datlow

(57) ABSTRACT

The present invention relates to a process for carrying out olefin ring-closing metathesis (RCM) wherein compressed carbon dioxide (gaseous, liquid or supercritical) acts as solvent for the liquid or solid reactant and the products obtained therefrom, while additionally one or more ionic liquids are introduced as the 2nd phase in which homogeneous olefin metathesis catalysts are immobilised.

20 Claims, 3 Drawing Sheets

PROCESS FOR CONTINUOUS RINGCLOSING METATHESIS IN COMPRESSED CARBONDIOXIDE

The present invention relates to a process for carrying out olefin ring-closing metathesis (RCM) wherein compressed carbon dioxide (gaseous, liquid or supercritical) acts as solvent for the liquid or solid reactant and the products obtained therefrom, while additionally one or more ionic liquids are introduced as the 2nd phase in which homogeneous olefin metathesis catalysts are immobilised.

BACKGROUND OF THE INVENTION

Ring-closing olefin metathesis (RCM) has in the mean time advanced to become one of the most successful synthesis methods by which cyclic structures of all sizes and with a plurality of functional groups can be efficiently synthesised. This property has made this transformation of substances a central tool in the modern chemistry of natural substances, which constitutes a reliable criterion for its exceptional usefulness in synthesis (a) R. H. Grubbs and S. Chang, *Tetrahedron*, 1998, 54, 4413; b) A. Fürstner, *Angew. Chem. Int. Ed.*, 2000, 39, 3012; c) S. J. Connon, S. Blechert, *Angew. Chem. Int. Ed.*, 2003, 42, 1900).

Hitherto, only homogeneous catalysts (predominantly Ru complexes) have been considered for the transformation of functionalised olefins, as they have a far higher group tolerance than their heterogeneous metal oxide-based analogues. However, the concentrations of the homogeneous catalysts used are typically in the one-digit molar percentage range, which makes it essential to separate them efficiently from the product for economic and toxicological reasons.

The state of the art is the immobilisation of the homogeneous catalysts on solid carrier materials which can be separated off by filtration after the reaction has taken place, or the separation and recycling of the homogeneous catalyst by multi-phase catalysis, a process in which the catalyst is immobilised in one phase (stationary phase) and the products may be obtained from the other phase (known as the mobile phase in the continuous process). Two special issues have already been published on the subject of two-phase catalysis and related technologies: a) *Catalysis Today* 1998, 42, issue 2; b) *Chem. Rev.* 2002, 102, October issue). The latter strategy has been very successfully implemented in the Shell Higher Olefin Process or in the Ruhrchemie-Rhône-Poulenc Process. The two processes are characterised in that only gaseous starting materials are used which are converted into liquid products. These can then be separated off as a phase in their own right.

However, this method is by no means generally applicable, as the chemical-physical properties of starting materials and corresponding target molecules are often very similar. This is true particularly of olefin ring-closing metathesis. In addition, reactants which are liquid and solid at ambient temperature—the aggregate states of nearly all fine chemicals—are far more difficult to react efficiently in multi-phase catalysis, essentially because an additional solvent has to be used. This is needed in order to intensify contact with the catalyst phase and produce a suitable concentration of the substrates at the reaction site. Precisely for efficiently performing ring-closing olefin metathesis both functions of the solvent are of fundamental importance for a high throughput and selectivity (cyclisation vs. oligomer formation). The incorporation of another solvent phase, however, leads to a number of problems:

1. The products have to be freed from the solvent, a process which generally exposes them to thermal loading, which often reduces the yield.
2. It often proves very difficult to remove the last traces of solvent from the product, and this is a particular problem for pharmaceutical production lines.
3. The widely used metathesis catalysts have insufficiently selective distribution coefficients for conventional two-phase systems (liquid-liquid systems), with the result that there is undesirable leaching of catalyst into the substrate/product phase. As a result of this extractive removal, not only is the activity of the catalytic system reduced but there is also contamination of the product with catalyst, which is unacceptable in many branches of fine chemistry.
4. Particularly the mobile solvent used for a continuous process must be extremely clean, as otherwise impurities from it build up in the catalytically active phase, and in this way catalyst deactivation may be accelerated. However, highly pure organic solvents are very expensive and hence uneconomical. There is also the factor than in ring-closing metathesis of rings of average size (8-11 ring members) and large size (greater than or equal to 12 ring members) it is essential to work with very high dilutions so as to counteract reactions of oligomerisation.
5. In view of their flammability and high volatility conventional solvents constitute an additional potential risk.

The aim of the present invention was therefore to solve the problems mentioned above and to provide a process which is suitable for the continuous olefin ring-closing metathesis of both liquid and solid substrates.

Supercritical carbon dioxide has already proved itself as a solvent for olefin metathesis reactions of a whole range of cyclisable substrates. It is not only very good value (even in highly pure form), non-toxic and non-flammable but also allows controlled manipulation of the monomer-oligomer equilibrium in RCM, by varying the fluid density used ((a) A. Fürstner, L. Ackermann, K Beck, H. Hori, D. Koch, K. Langemann, M. Liebl, C. Six, W. Leitner, *J. Am. Chem. Soc.* 2001, 123, 9000-9006, b) Fürstner et al., Selective Olefin Metathesis of Bifunctional or Polyfunctional Substrates in compressed Carbon Dioxide as Reaction Medium, U.S. Pat. No. 6,348,551; c) DeSimone et al., Olefin Metathesis Reactions in Carbon Dioxide Medium, U.S. Pat. No. 5,840,820). When compressed carbon dioxide is used on its own as the reaction medium, two properties in particular are problematic for the ring-closing olefin metathesis.

1. On the one hand, the supercritical carbon dioxide does not have good dissolving properties on the currently most active metathesis catalysts, with the result that the conversion rates are correspondingly low. Quite apart from olefin metathesis this has led to the development of homogeneous catalysts with solubilising perfluorinated chains ((a) S. Kainz, D. Koch, W. Baumann, W. Leitner, *Angew. Chem. Int. Ed. Engl.* 1997, 36, 1628-1630; b) Holmes et al., Use of Compressed $CO_2$ in Chemical Reactions, U.S. Pat. No. 6,458,985 B1). However, such catalysts are complicated to synthesise and are therefore very expensive.
2. The solubility of the currently most active metathesis catalysts under reaction conditions which are suitable for efficiently reacting non-volatile substrates is still high enough to require separation of the catalyst from the product. But this cannot be done without additional adjuvants in subsequent processes. This is also the reason why immobilisation on a solid phase was developed for reactions in compressed carbon dioxide, the solid phase containing both $CO_2$-philic and $CO_2$-phobic parts of the molecule, so as on the one hand to achieve good transportation of the substance at the catalytically active centres while on the other hand ensuring efficient separation. (DeSimone et al., Carbon Dioxide-Soluble Polymers and Swellable Polymers for Carbon Dioxide Applications, U.S. Pat. No. 6,747,179 B1). As a limiting factor it must be stated, however, that the catalytic effectiveness of this concept is in no way characterised in the above-mentioned patent.

Ionic liquids are also described in the chemical literature as potential reaction media for carrying out olefin ring-closing metathesis reactions. Their major advantage is in their lack of volatility below their decomposition temperature and in their non-flammability. In addition, many examples are immiscible with conventional solvents, thus enabling the product to be easily isolated by extraction ((a) R. C. Buijsman, E. van Vuuren, J. G. Sterrenburg, Org. Lett. 2001, 3, 3785-3787, b) Gürtler et al., α,ω-Diene Metathesis in the Presence of Ionic Liquids, U.S. Pat. No. 6,756,500 B1). The most widely used Grubbs catalysts however exhibit significant leaching during extractive working up with conventional organic solvents, with the result that they can be recycled a maximum of once or twice. Building on this experience, in two independent studies imidazolium fragments were integrated in the most active catalyst structures currently known, which for the first time synthesised a precatalyst which can be recycled in ionic liquids (a) N. Audic, H. Clavier, M. Mauduit, J.-C. Guillemin, J. Am. Chem. Soc. 2003, 125, 9248-9249; b) Q. Yao, Y. Zhang, Angew. Chem Int. Ed. 2003, 42, 3395-3398). Apart from the use of highly volatile, combustible and in some cases toxic solvents for the extractive working up, however, there are also other disadvantages:

1. In a fast chemical reaction at the catalyst centre (which is dissolved in the ionic liquid) the mass transfer frequently limits the speed of the reaction as a whole. This problem is generally considerably more serious than in reactions in the two-phase system with two organic phases or one organic and one aqueous phase, as the relatively high viscosity of the ionic liquid leads to a low coefficient of diffusion and relatively large droplets in the stirred system. Both these effects undesirably influence the mass transfer of the educt to the catalyst centre.
2. Ionic liquids are significantly more expensive than water and the majority of organic solvents. From the point of view of the industrial user, this demands total recovery not only of the transition metal catalyst used but also of the ionic liquid used in the system. Against this background, the greater or lesser cross-solubility of ionic liquids in the organic educts and products is problematic, and is particularly serious when educts and products themselves have a certain polarity. In a continuous process, there may thus be a constant loss of ionic liquid and catalyst into the products.

In 1999 the Brennecke and Beckman research groups described the phase characteristics of two-phase mixtures of ionic liquids with supercritical carbon dioxide (L. A. Blanchard, D. Hancu, E. J. Beckman, J. F. Brennecke, Nature 1999, 399, 28-29). They were able to show that supercritical $CO_2$ dissolves easily in some ionic liquids, while the same ionic liquids have no detectable solubility in supercritical $CO_2$. Moreover, in this publication, the authors described the possibility of extracting high-boiling substances from ionic liquids, using supercritical $CO_2$. No contamination of the extract with ionic liquids could be detected.

The Jessop working group used extraction with supercritical $CO_2$ to isolate the products from ionic liquids following a hydrating reaction with neutral ruthenium catalysts (R. A. Brown, P. Pollett, E. McKoon, C. A. Eckert, C. L. Liotta, P. G. Jessop, J. Am Chem. Soc. 2001, 123, 1254). This concept was expanded by Baker and Tumas, who described the successful hydrogenation of cyclohexene and 1-decene using the neutral Wilkinson catalyst $RhCl(PPh_3)_3$ in the two-phase system of [BMIM][$PF_6$]/supercritical carbon dioxide. However, comparison tests carried out by these authors showed that in the presence of supercritical $CO_2$, generally lower or, at best, equally high activities are found for the catalysts. The conversion rates in the [BMIM][$PF_6$]/supercritical carbon dioxide system correspond in favourable cases to the values achieved in the [BMIM][$PF_6$]/n-hexane system (F. Liu, M. B. Abrams, R. T. Baker, W. Tumas, Chem. Commun. 2001, 433). Another catalytic study in a two-phase system consisting of supercritical carbon dioxide and an ionic liquid was published by Cole-Hamilton and colleagues (Cole-Hamilton et al., Catalysis in an Ionic Fluid, Supercritical Fluid Two Phase System, WO 02/02218 A1; M. F. Sellin, P. B. Webb, D. J. Cole Hamilton, Chem Commun. 2001, 781). The group investigated the hydroformylation of 1-hexene, 1-octene and 1-nonene with anionic Rh complexes. However, their method is restricted to systems in which there is at least one reactant which is gaseous under normal conditions.

Figure 1:
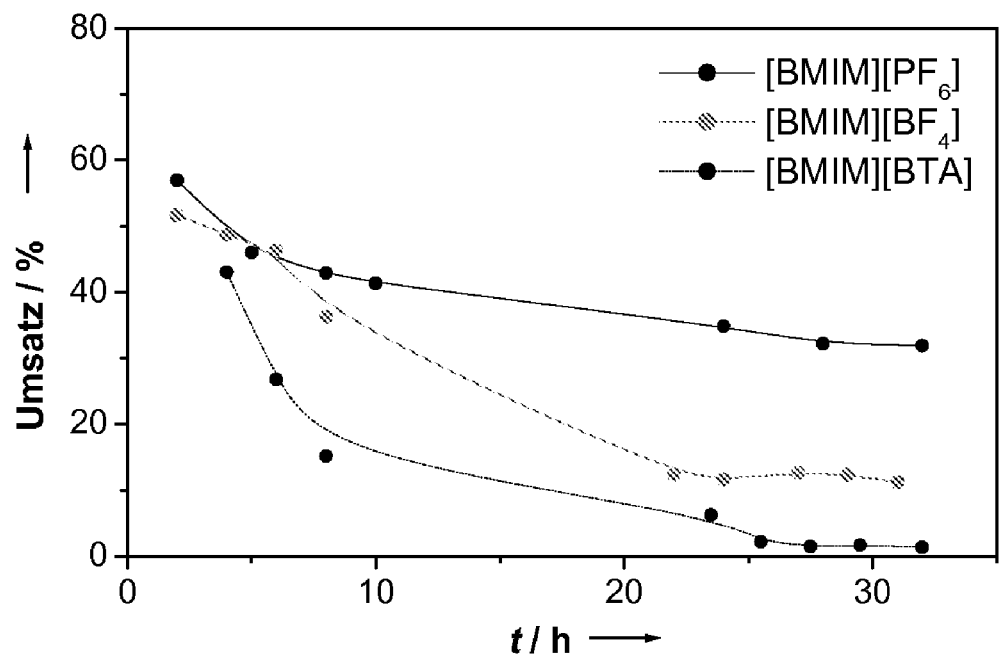
FIG. 1. Conversion-time profile during continuous RCM of 1,7-octadiene 10 using catalyst 1 and varying the anionic structure of the [BMIM]-based ILs (Ionic Liquids). Experimental conditions: T=40° C., p=170 bar.
Figure 2:
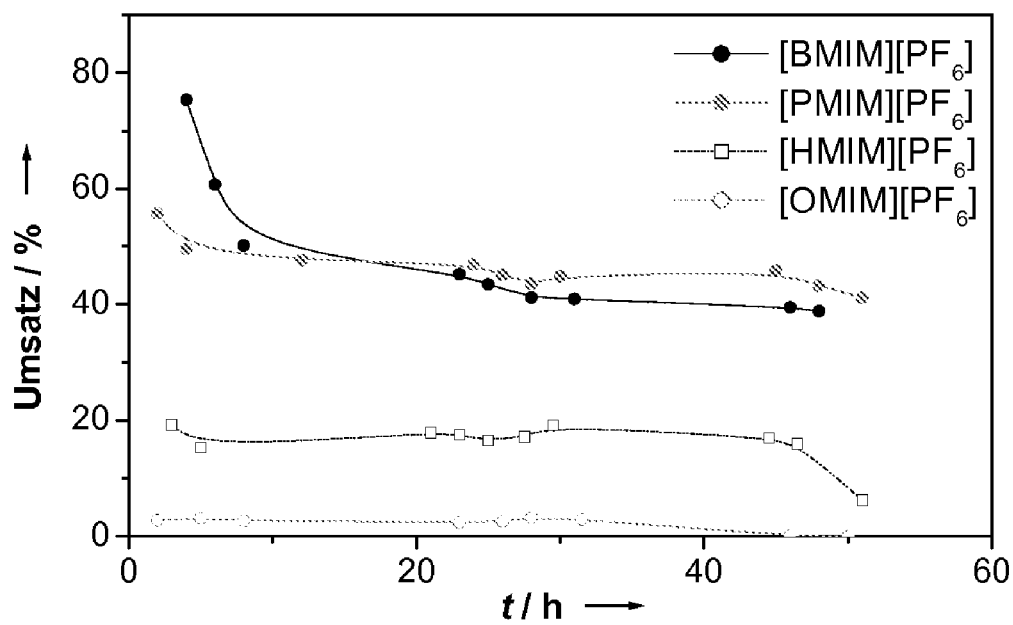
FIG. 2. Conversion-time profile during continuous RCM of 1,7-octadiene 10 using catalyst 1 and varying the alkyl group chain length of imidazolium-hexafluorophosphate-based ILs. M=methyl, B=n-butyl, P=n-pentyl, H=n-hexyl, O=n-octyl. Experimental conditions: T=40° C., p=110 bar.
Figure 3:
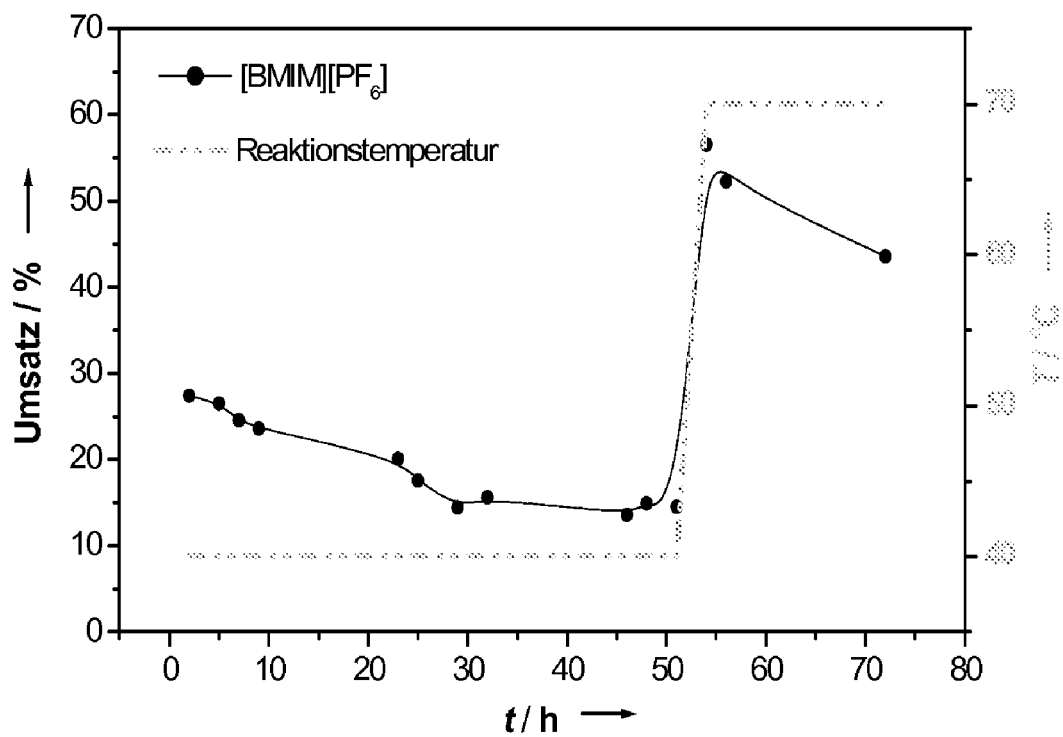
FIG. 3. Influence of the reaction temperature on the continuous RCM of 1,7-octadiene 10 using catalyst 2. Experimental conditions: p=170 bar, IL=[BMIM][$PF_6$].
Figure 4:
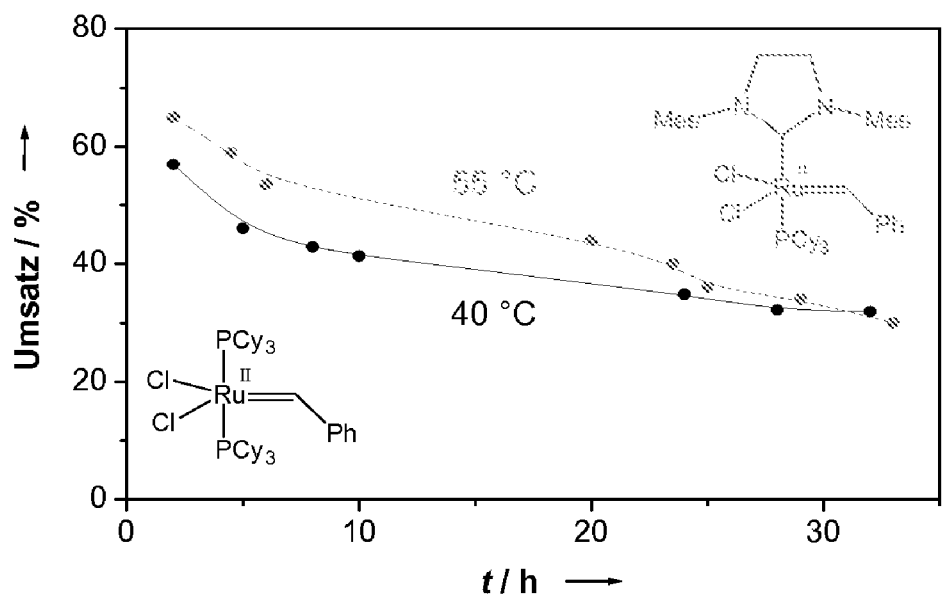
FIG. 4. Comparison of the conversion effect of catalysts 1 and 2 on the continuous RCM of 1,7-octadiene 10 under optimum conditions. Experimental conditions: p=170 bar, IL=[BMIM][$PF_6$].

Definition of Terms in the Figures:
Umsatz=conversion
Reaktionstemperatur=reaction temperature
Edukt-beladener $CO_2$-Strom=educt-charged $CO_2$ current
SFC-Pumpe=SFC pump
Edukt-Reservoir=educt reservoir
Kohlendioxid=carbon dioxide
unbeladener $CO_2$-Strom=uncharged $CO_2$ current

DETAILED DESCRIPTION OF THE INVENTION

The present process according to the invention, by contrast, is characterised in that a liquid or solid substrate is dissolved in the compressed carbon dioxide and by vigorous stirring is brought into intimate contact, and thereby reacted, with the second, liquid phase, the catalyst-containing ionic liquid in which a plurality of substrates, products and metal complex metathesis catalysts dissolve homogeneously. The reaction temperature (between −50 and 300° C., preferably between −20 and 150° C.) and the overall pressure (between 10 and 1000 bar, preferably between 50 and 500 bar) is selected so that the density of the $CO_2$ phase is between 0.2 and 1.2 g/ml. Because of the high molecular weight, low volatility and high polarity of the metathesis catalyst the latter does not dissolve in the compressed carbon dioxide phase in the process according to the invention and is thus effectively immobilised in the IL phase in the multi-phase process under suitable reaction conditions.

The present invention therefore relates to a process which is suitable for the continuous olefin ring-closing metathesis of both liquid and solid substrates and comprises supercritical carbon dioxide, one or more ionic liquids, a homogeneous catalyst and a substrate which can be cyclised by olefin metathesis.

It has been found that, surprisingly, the process according to the invention is outstandingly suitable for the continuous olefin ring-closing metathesis of both liquid and solid substrates. Particularly preferably, slightly polar to non-polar substrates with molecular weights of $\leq 700$ g/mol can be reacted, without the presence of strong Lewis-basic centres. Depending on the substrate structure the process according to the invention may be used to produce carbo- and heterocycles of a freely selectable ring size n (n$\geq$5), including rings of average size (8-11 ring members) and large size (greater than or equal to 12 ring members). Particularly preferably the process according to the invention can be used to synthesise rings with between 5-7 ring members and large rings ($\geq$12 ring members).

Suitable catalysts for the process according to the invention are in particular the neutral and ionic pre-catalysts 1, 4, 5, 6, 7, 8 and 9 shown, although this does not imply any restriction to the scope of the invention.

1

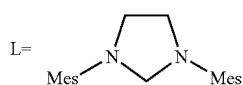

2

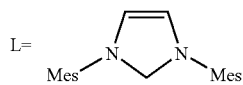

3

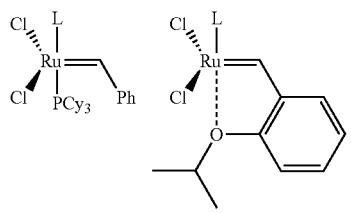

4

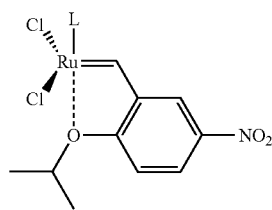

5

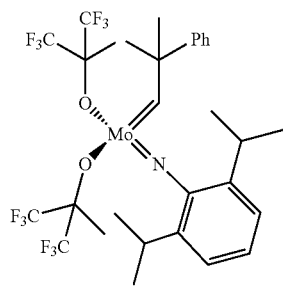

6

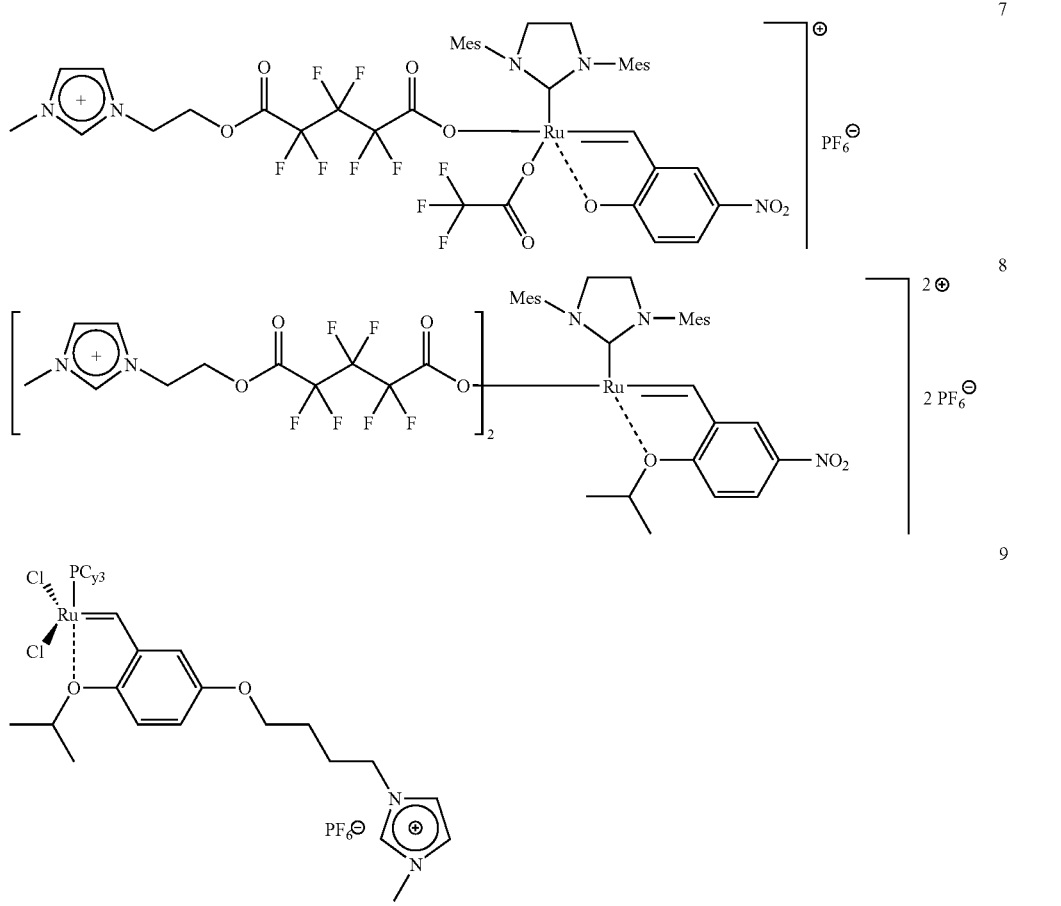

Mes = 2,4,6-Trimethylphenyl
Cy = Cyclohexyl

Preferably in this process a catalyst of formula A is used;

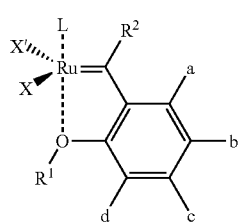

wherein
X and X' denote anionic ligands;
L denotes a neutral ligand;
a, b, c, d independently of one another denote H, halogen, $NO_2$, $C_{1-6}$-alkyl, $CO—R^{a-d}$, $SO_2—R^{a-d}$, $PO(R^{a-d})_2$, $C_{1-6}$-alkoxy or aryl, while aryl may optionally be substituted by a group selected from among $C_{1-6}$-alkyl and $C_{1-6}$-alkoxy;
$R^{a-d}$ denotes $C_{1-8}$-alkyl, $C_{3-6}$-cycloalkyl or aryl, optionally substituted by a group selected from among F, Cl, Br, I, $C_{1-6}$-alkyl, $C_{1-6}$-alkoxy, $NO_2$, CN, $CF_3$, $OCF_3$ or $C_{1-6}$-alkoxycarbonyl
$R^1$ denotes $C_{1-6}$-alkyl, $C_{1-6}$-haloalkyl, $C_{3-6}$-cycloalkyl, $C_{7-18}$-aralkyl or a group of formula A1, wherein the asterisk indicates the point of attachment to the molecule and $R^{11}$ denotes $C_{1-6}$-alkyl, $C_{3-6}$-cycloalkyl, $C_{7-18}$-aralkyl, aryl;
$R^{12}$ denotes H, $C_{1-6}$-alkyl, $C_{3-6}$-cycloalkyl, $C_{7-18}$-aralkyl, aryl;
$R^2$ denotes H, $C_{1-6}$-alkyl, $C_{2-6}$-alkenyl, $C_{2-6}$-alkynyl or aryl;
particularly preferably
$R^1$ denotes —$C_{1-6}$-alkyl, —$C_{1-6}$-haloalkyl, —$C_{3-6}$-cycloalkyl or —$C_{7-18}$-aralkyl
and most preferably
a, c, d denote H; and
b denotes —$NO_2$.
Also preferred is the process described above wherein a catalyst of formula A is used and
L denotes a ligand of formula $P(R^4)_3$, wherein $R^4$ denotes $C_{1-6}$-alkyl, cycloalkyl or aryl;
particularly preferably L denotes a ligand of formula $L^1$, $L^2$, $L^3$ or $L^4$,

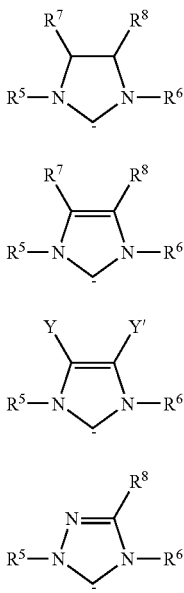

wherein

R⁵ and R⁶ independently of one another denote H, C$_{1-6}$-alkyl or aryl;

R⁷ and R⁸ independently of one another denote H, C$_{1-6}$-alkyl, C$_{2-6}$-alkenyl or aryl; or R⁷ and R⁸ together form a 3- or 4-membered alkylene bridge; and Y and Y' denote halogen.

The term "C$_{1-8}$-alkyl" (including those which are part of other groups) denotes branched and unbranched alkyl groups with 1 to 8 carbon atoms, while the term "C$_{1-6}$alkyl" denotes branched and unbranched alkyl groups with 1 to 6 carbon atoms and the term "C$_{1-4}$alkyl" denotes branched and unbranched alkyl groups with 1 to 4 carbon atoms. Preferred are alkyl groups with 1 to 4 carbon atoms. Examples include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. are optionally also used for the above-mentioned groups. Unless otherwise stated, the definitions propyl, butyl, pentyl and hexyl include all possible isomeric forms of the groups in question. Thus, for example, propyl includes n-propyl and iso-propyl, butyl includes iso-butyl, sec-butyl and tert-butyl etc.

The term "C$_{2-6}$-alkenyl" (including those which are part of other groups) denotes branched and unbranched alkenyl groups with 2 to 6 carbon atoms and the term "C$_{2-4}$-alkenyl" denotes branched and unbranched alkenyl groups with 2 to 4 carbon atoms, provided that they have at least one double bond. Preferred are alkenyl groups with 2 to 4 carbon atoms. Examples include: ethenyl or vinyl, propenyl, butenyl, pentenyl, or hexenyl. Unless otherwise stated, the definitions propenyl, butenyl, pentenyl and hexenyl include all possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

The term "C$_{2-6}$-alkynyl" (including those which are part of other groups) denotes branched and unbranched alkynyl groups with 2 to 6 carbon atoms and the term "C$_{2-4}$-alkynyl" denotes branched and unbranched alkynyl groups with 2 to 4 carbon atoms, provided that they have at least one triple bond. Preferred are alkynyl groups with 2 to 4 carbon atoms. Examples include: ethynyl, propynyl, butynyl, pentynyl or hexynyl. Unless otherwise stated, the definitions propynyl, butynyl, pentynyl and hexynyl include all possible isomeric forms of the groups in question. Thus, for example, propynyl includes 1-propynyl and 2-propynyl, butynyl includes 1-, 2- and 3-butynyl, 1-methyl-1-propynyl, 1-methyl-2-propynyl etc.

The term "C$_{1-6}$-alkoxy" (including those which are part of other groups) denotes branched and unbranched alkoxy groups with 1 to 6 carbon atoms and the term "C$_{1-4}$-alkoxy" denotes branched and unbranched alkoxy groups with 1 to 4 carbon atoms. Preferred are alkoxy groups with 1 to 4 carbon atoms. Examples include: methoxy, ethoxy, propoxy, butoxy or pentoxy. In some cases the abbreviations MeO, EtO, PrO, etc. may be used for the above-mentioned groups. Unless otherwise stated, the definitions propoxy, butoxy and pentoxy include all possible isomeric forms of the groups in question. Thus, for example, propoxy includes n-propoxy and iso-propoxy, butoxy includes iso-butoxy, sec-butoxy and tert-butoxy etc.

The term "C$_{3-6}$-cycloalkyl" (including those which are part of other groups) denotes cyclic alkyl groups with 3 to 6 carbon atoms. Examples include: cyclopropyl, cyclobutyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

The term "aryl" (including those which are part of other groups) denotes aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

The term "C$_{7-18}$-aralkyl" (including those which are part of other groups) denotes branched and unbranched alkyl groups with 1 to 8 carbon atoms which are substituted by an aromatic ring system with 6 or 10 carbon atoms, while the term "C$_{7-11}$-aralkyl" accordingly denotes branched and unbranched alkyl groups with 1 to 4 carbon atoms which are substituted by an aromatic ring system with 6 carbon atoms. Examples include: benzyl, 1- or 2-phenylethyl. Unless otherwise stated, the aromatic groups may be substituted by one or more groups selected from among methyl, ethyl, iso-propyl, tert-butyl, hydroxy, fluorine, chlorine, bromine and iodine.

Carbon dioxide is used in the process according to the invention in gaseous, supercritical or liquid form. Densities of between 0.2 g/ml and 1.2 g/ml, preferably between 0.3 g/ml and 0.9 g/ml, should be used.

In the process according to the invention the ionic liquids used may be salts or mixtures of salts of formula$[A]_n^+[Y]^{n-}$ where n=1 or 2, having a melting point <100° C., the anion $[Y]^{n-}$ is selected from among tetrafluoroborate ($[BF_4]^-$), tetrachloroborate ($[BCl_4]^-$), hexafluorophosphate ($[PF_6]^-$), hexafluoroantimonate ($[SbF_6]^-$), hexafluoroarsenate ($[AsF_6]^-$), tetrachloroaluminate ($[AlCl_4]^-$), trichlorozincate ($[ZnCl_3]^-$), dichlorocuprate ($[CuCl_2]^-$), sulphate ($[SO_4]^{2-}$), carbonate ($[CO_3]^{2-}$), fluorosulphonate, [R'—COO]⁻, [R'—SO$_3$]⁻, [R'—SO$_4$]⁻, [tetrakis-(3,5-bis-(trifluoromethyl)-phenyl)borate] ($[BARF]^-$) and $[(R'—SO_2)_2N]^-$, while R' is a straight-chain or branched aliphatic or alicyclic alkyl containing 1 to 12 carbon atoms or a C$_5$-C$_{18}$-aryl, C$_5$-C$_{18}$-aryl-C$_1$-

$C_6$-alkyl or $C_1$-$C_6$-alkyl-$C_5$-$C_{18}$-aryl group, which may be substituted by halogen atoms, the cation [A]$^+$ is selected from among quaternary ammonium cations of general formula [NR$^1$R$^2$R$^3$R$^4$]$^+$,
phosphonium cations of general formula [PR$^1$R$^2$R$^3$R$^4$]$^+$,
imidazolium cations of general formula

while the imidazole nucleus may be substituted by at least one group which is selected from $C_1$-$C_6$-alkyl, $C_1$-$C_6$-alkoxy, $C_1$-$C_6$-aminoalkyl, $C_5$-$C_{12}$-aryl or $C_5$-$C_{12}$-aryl-$C_1$-$C_6$-alkyl groups,
pyridinium cations of general formula

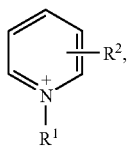

while the pyridine nucleus may be substituted by at least one group which is selected from $C_1$-$C_6$-alkyl, $C_1$-$C_6$-alkoxy, $C_1$-$C_6$-aminoalkyl, $C_5$-$C_{12}$-aryl or $C_5$-$C_{12}$-aryl-$C_1$-$C_6$-alkyl groups,
pyrazolium cations of general formula

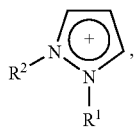

while the pyrazole nucleus may be substituted by at least one group which is selected from $C_1$-$C_6$-alkyl, $C_1$-$C_6$-alkoxy, $C_1$-$C_6$-aminoalkyl, $C_5$-$C_{12}$-aryl or $C_5$-$C_{12}$-aryl-$C_1$-$C_6$-alkyl groups and
triazolium cations of general formula

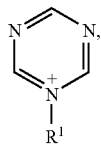

while the triazole nucleus may be substituted by at least one group which is selected from $C_1$-$C_6$-alkyl, $C_1$-$C_6$-alkoxy, $C_1$-$C_6$-aminoalkyl, $C_5$-$C_{12}$-aryl or $C_5$-$C_{12}$-aryl-$C_1$-$C_6$-alkyl groups,
while the groups R$^2$, R$^3$, R$^4$ are selected independently of one another from the group comprising
hydrogen;
straight-chain or branched, saturated or unsaturated, aliphatic or alicyclic alkyl groups with 1-20 carbon atoms;
heteroaryl, heteroaryl-$C_1$-$C_6$-alkyl groups with 3 to 8 carbon atoms in the heteroaryl group and at least one heteroatom, selected from N, O and S, which may be substituted by at least one group selected from $C_1$-$C_6$-alkyl groups and/or halogen atoms;
aryl, aryl $C_1$-$C_6$-alkyl groups with 5 to 12 carbon atoms in the aryl group which may optionally be substituted by at least one $C_1$-$C_6$-alkyl group and/or a halogen atom;
and the group R$^1$ denotes
straight-chain or branched, saturated or unsaturated, aliphatic or alicyclic alkyl groups with 1-20 carbon atoms;
heteroaryl, heteroaryl-$C_1$-$C_6$-alkyl groups with 3 to 8 carbon atoms in the heteroaryl group and at least one heteroatom, selected from N, O and S, which may be substituted by at least one group selected from $C_1$-$C_6$-alkyl groups and/or halogen atoms;
aryl, aryl $C_1$-$C_6$-alkyl groups with 5 to 12 carbon atoms in the aryl group which may optionally be substituted by at least one $C_1$-$C_6$-alkyl group and/or a halogen atom.

In batch operation, after the reaction has ended, the products may be removed from the catalyst by extraction with suitable solvents. Expediently, this extraction is carried out directly using carbon dioxide, while the density may be identical to that of the reaction or may be varied within the range specified so as to achieve the fastest possible extraction. The catalyst may be recovered directly and used again.

The compressed carbon dioxide used in the process according to the invention thanks to its special chemical-physical properties allows the process to operate continuously, in highly efficient manner. In order to do this, liquid or solid substrates are homogeneously mixed with compressed carbon dioxide in a preceding reactor (phase 1). Carbon dioxide may be used in gaseous, supercritical or liquid form, the density being in the range between 0.1 g/ml and 1.2 g/ml, preferably between 0.3 g/ml and 0.9 g/ml. This mixture is conveyed into the reactor in the direction of flow; the reactor already contains the ionic liquid containing the catalyst (phase 2) at the desired reaction temperature. From the supernatant compressed carbon dioxide phase (phase 1) the dissolved product is separated from the carbon dioxide by controlled lowering of the pressure and/or by varying the temperature using a suitable valve to temperatures between −60 and 200° C. In this way the product may be isolated directly from the carbon dioxide current.

The following Examples illustrate the procedure for both batch and continuous operation using prototypical substrates. The advantages of the new process are clear, particularly: a) high selectivity with a high conversion of differently substituted substrates and b) high long-term stability.

EXAMPLES

1. RING-CLOSING METATHESIS OF 1,7-OCTADIENE

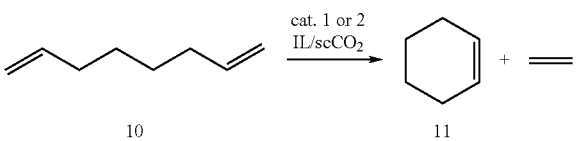

Diagram 1. RCM of 1,7-octadiene, IL = Ionic Liquid, scCO$_2$ = supercritical carbon dioxide 1.1 Batch Process In a typical experiment a 10 ml V4A stainless steel autoclave, fitted with Teflon seals, thick-walled boron silicate inspection glasses, a Teflon-coated magnetic stirrer core, a thermocouple, a pressure sensor and a valve, is filled with 5 mg of the Grubbs catalyst 1 or 2, 2.5 ml of an ionic liquid (purified by column chromatography) and 100 μl of 1,7-octadiene 10 under inert conditions. The reactor was charged with $CO_2$ and heated to 40° C. with continuous stirring. After one hour's reaction the reactor was vented through a heated needle valve, while the reaction mixture was separated from the gas current in a subsequent cold trap thermostatically controlled to −60° C. The ionic liquid was extracted with n-pentane, the extract was combined with the contents of the cold trap and analysed by gas chromatography. The results obtained are listed in Table 1.

TABLE 1

Results of the batch experiments on ring-closing metathesis of 1,7-octadiene

| Ionic liquid | Catalyst | Conversion | Selectivity |
|---|---|---|---|
| [BMIM][PF$_6$] | 1 | >99% | >99% |
| | 2 | >99% | >99% |
| [BMIM][BF$_4$] | 1 | >99% | >99% |
| | 2 | >99% | >99% |
| [BMIM][BTA][1] | 1 | >99% | >99% |
| | 2 | >99% | >99% |

[1]BTA = bis(trifluoromethylsulphonimide)

1.2 Continuous Process

In a typical experiment a 10 ml V4A stainless steel autoclave, fitted with Teflon seals, thick-walled boron silicate inspection glasses, a Teflon-coated magnetic stirrer core, a thermocouple, a pressure sensor and an inlet and outlet valve, is filled with 80 mg of the Grubbs catalysts 1 or 2 and 2.5 ml of an ionic liquid (purified by column chromatography) under inert conditions. The reactor was charged with $CO_2$ and brought to the required reaction temperature with continuous stirring. With the aid of a compressor, $CO_2$ was piped through the ionic liquid at the desired pressure using a 1/16" capillary. Using an HPLC pump, 1,7-octadiene 10 was added to the $CO_2$ current through a T-connector immediately in front of the reactor entrance (flow rate=1 ml h$^{-1}$). Using a heatable needle valve the total flow at the reactor exit was limited to 5-7 l h$^{-1}$ (volume of gas at normal pressure, measured with a gas meter). The reaction mixture was separated from the gas current in a cold trap which was thermostatically controlled to −60° C. The cold trap was replaced after the time intervals specified in the conversion time profiles in FIGS. 1 to 4 and its contents were analysed by gas chromatography.

2. RING CLOSING METATHESIS (RCM) OF COMPOUND 12

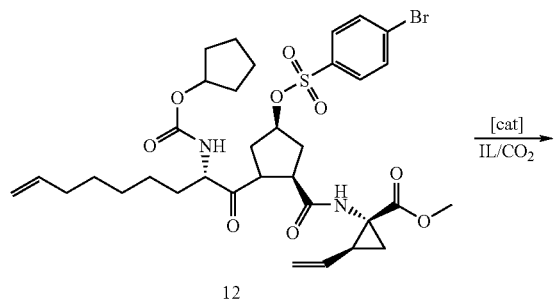

12

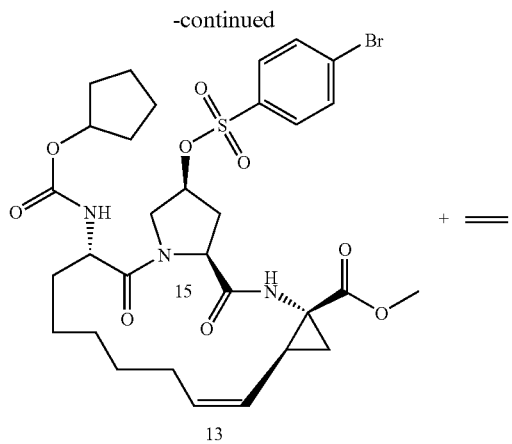

13

2.1 Conventional Method 2.1.1 Carrying Out the Metathesis Reaction and Working Up 33.0 g of a 33.4% toluene solution of 12 (14.9 mmol) were dissolved in 1270 ml of toluene and degassed over a period of 1 h by passing nitrogen through. Under a nitrogen atmosphere the solution was heated to 80° C. and then 0.040 g of Grela's catalyst 5 (0.059 mmol) was added as a solid. After one hour's reaction another 0.026 g of catalyst 5 (0.039 mmol) were added and the reaction mixture was stirred for another 60 min until conversion was complete.

The reaction mixture was cooled to 60° C., 30 ml of the THP solution described below were added and the mixture was stirred for 6 h at 60° C. After the solution had cooled to ambient temperature, the mixture was washed twice with 59 ml of water, 50 ml of 2% hydrochloric acid, 50 ml of a 5% sodium hydrogen carbonate solution and finally washed with 59 ml of water. Approximately 1100 ml of the toluene was distilled off at a maximum temperature of 50° C. under reduced pressure and the residue was purified with 0.56 g activated charcoal at 50° C. for 2 h. After separation of the activated charcoal by filtration the solution was concentrated down to 31 ml. 2 ml of this solution was added dropwise over a period of 30 min to 315 ml of cold (0-7° C.) methylcyclohexane and the mixture was stirred for 30 min at this temperature. Then the remainder of the toluene solution was added dropwise over a period of 30 min at 0-7° C. The resulting suspension was stirred for 30 min and the precipitate was isolated by filtration. The white product was washed three times with 20 ml cold (0-5° C.) methylcyclohexane and dried in vacuo at 35° C.

Yield (by weight): 11.1 g Yield (according to analysis): 9.0 g (12.7 mmol), 85% Purity: 90% (HPLC area)

2.1.2 Preparation of the THP Solution

A solution of 8.9 g tetrakishydroxymethylphosphonium chloride (80%, 37.4 mmol) in 19 ml degassed isopropanol was cooled to 0-10° C. under a nitrogen atmosphere and 4.7 g of a 45% potassium hydroxide solution (37.4 mmol) was added within 5 min, while the mixture was cooled to ensure that the reaction temperature did not rise above 27° C. After the solution had been stirred for a further 30 min under a nitrogen atmosphere, the suspension formed was filtered and the inorganic residue was washed with 8 ml degassed isopropanol. The combined isopropanol solutions were stored under a nitrogen atmosphere until required.

2.2 Batch Method

In a typical experiment a 10 ml V4A stainless steel autoclave was used which was fitted with Teflon seals and thick-walled boron silicate inspection glasses, a Teflon-coated magnetic stirrer core, a thermocouple, a pressure sensor and a valve. First, 16 mg of 12 were stuck with a little toluene to the upper part of an inspection glass, the reactor was assembled and the toluene was eliminated under a fine vacuum. 3 ml of [BMIM][PF$_6$], which had been purified by column chromatography (silica gel, eluant dichloromethane) beforehand, and 1 ml of a dichloromethane solution containing 1.5 mg of the Grela's catalyst 5, were stirred for 5 minutes and then the dichloromethane was distilled off in vacuo. 2.5 ml of this solution was added to the reactor through an opening in the upper reactor wall under inert conditions, in such a way that this phase did not make contact with the substrate 12 adhering to the glass. After the reactor had reached the reaction temperature of 70° C., 400 bar of carbon dioxide were compressed in (t$_0$) using an SFC injection pump, with constant stirring. After one hour's reaction the autoclave was cooled with cold water and vented. The IL phase was extracted 2× with 2 ml of toluene and the autoclave was rinsed 2× with 2 ml of toluene. The combined toluene phases were filtered, the toluene was distilled off in vacuo and the oil remaining (16 mg) was analysed by HPLC. A product/educt ratio of 59:1 was achieved, while the two peaks together made up 81% of the total peak area.

2.3 Continuous Method

Figure 5:
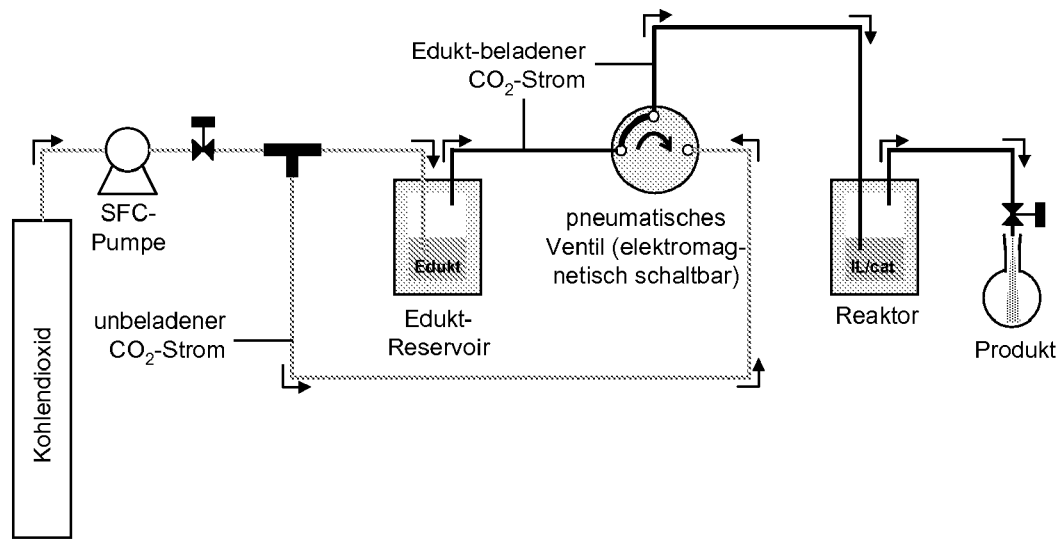
FIG. 5. Schematic representation of the partial experimental set-up including an electromagnetically operated 3-way valve which carries an uncharged and a substrate-charged $CO_2$ current (shown here) into the reactor according to a timed programme.

In a typical experiment two 10 ml V4A stainless steel autoclaves were used, analogous to those in the batch experiment (see 2.1), except that they were additionally fitted with both an inlet and an outlet valve. These were connected as shown in FIG. 5 by a pneumatically operated electromagnetically controlled 2-position three-way valve.

Figure 6:
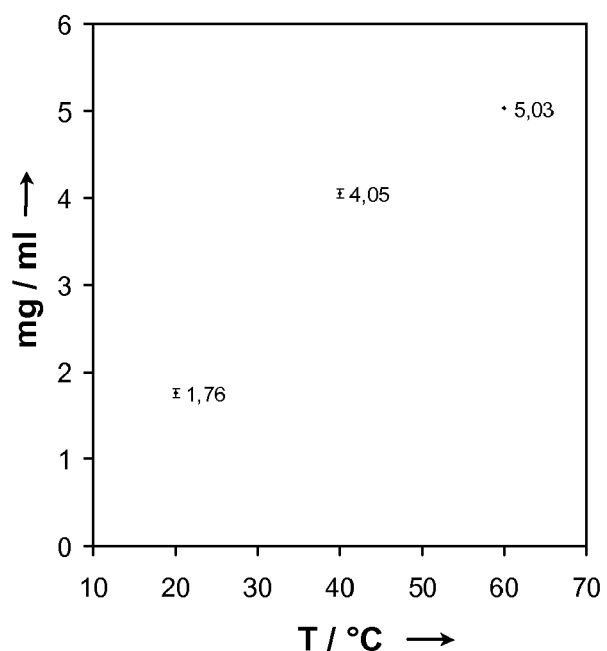
FIG. 6. Amount of 12 absorbed per ml of compressed $CO_2$ phase as a function of the reservoir temperature. In each case the amount of 12 which was taken up by 100 ml compressed $CO_2$ (400 bar) at the corresponding reservoir temperature was quantified.

About 2.5 g of educt 12 were added to the autoclave, which is termed the educt reservoir. In the reactor there were 2.5 ml of ionic liquid which had been combined with 20-60 mg Grela's catalyst 5, as described under 2.1. The substrate concentration in the mobile CO$_2$ phase and hence at the reaction site as well was precisely determined by means of two parameters: on the one hand, the temperature of the educt reservoir, the dependency of which on the educt saturation concentration is shown in FIG. 6, the experiment being carried out at a standard temperature of 20° C., corresponding to a charge amount of 1.76 mg of substrate 12 per ml of compressed CO$_2$ phase. On the other hand, by the electromagnetically controlled three-way valve shown in FIG. 5, which according to a timed programme allows an uncharged and a substrate-charged CO$_2$ current into the reactor (T=70° C.). The ratios of charged to uncharged CO$_2$ phase selected were between 1:0 and 0.1:1.

The flow rate at a constant pressure of p=400 bar (by SFC pump adjustment) was regulated using a heatable needle valve (T=60620 C.), and flow rates of between 100 and 1000 µl min$^{-1}$ compressed CO$_2$ phase were achieved. The amount of compressed carbon dioxide used was read off on the SFC injection pump, and from this the amount of substrate added was calculated. The vessels holding the weighed-out product were replaced after the measuring intervals shown in the data in Table 2, counter-weighed and their contents were analysed by HPLC.

TABLE 2

Results of continuous experiments (batch experiments as a comparison).

| No | m (12)[a] | CO$_2$-flow rate/µl min$^{-1}$ | IL | m (cat) | m (extract) | product/educt |
|---|---|---|---|---|---|---|
| 0 | 16 mg | batch | [BMIM][PF$_6$] | 1.5 mg | n.g. | 59 (Σ 81% PF) |
| 1 | 200 mg | first runnings | [BMIM][PF$_6$] | 7.9 mg | n.g. | 0.53 (Σ 28% PF) |
|   |        | 700-1200       |                 |        | n.g. | 3.12 (Σ 87% PF) |
| 2 | 22 mg | 320-350 | [BMIM][PF$_6$] | 19.5 mg | n.g. | 1.18 (Σ 32% PF) |
|   | 46 mg | 160-220 |                |         | 2.8 mg | 1.48 (Σ 62% PF) |
|   |       | 600-660 |                |         |        |                 |
|   | 26 mg | 200-250 |                |         | 1.4 mg | 1.41 (Σ 68% PF) |
|   | 30 mg | 250-320 |                |         | 3.1 mg | 0.75 (Σ 93% PF) |
|   | 26 mg | 250-300 |                |         | 3.2 mg | 0.33 (Σ 91% PF) |
|   | 27 mg | 250-300 |                |         | 3.0 mg | 0.19 (Σ 95% PF) |
|   | 21 mg | 250-300 |                |         | 6.5 mg | 0.13 (Σ 95% PF) |
| 3 | 30 mg | 350-400 | [BMIM][BTA] | 60.0 mg | 2.5 mg | 0.28 (Σ 28% PF) |
|   | 47 mg | 350-480 |             |         | 2.0 mg | 2.41 (Σ 21% PF) |
|   | 53 mg | 350-480 |             |         | 2.1 mg | 3.29 (Σ 32% PF) |
|   |       | residual pressure |        |         | n.g.   | 2.85 (Σ 13% PF) |
|   | 49 mg | 370-430 |             |         | 4.5 mg | 1.08 (Σ 62% PF) |
|   | 37 mg | 370-430 |             |         | 3.7 mg | 0.45 (Σ 75% PF) |
|   | 129 mg | 1000-1200 |           |         | 37.4 mg | 0.13 (Σ 92% PF) |
|   | 39 mg | 660-700 |             |         | 12.5 mg | 0.09 (Σ 92% PF) |
|   | 37 mg | 230-280 |             |         | 12.1 mg | 0.07 (Σ 93% PF) |
|   | 29 mg | 230-280 |             |         | 11.0 mg | 0.06 (Σ 94% PF) |
|   | 34 mg | 230-280 |             |         | 14.3 mg | 0.05 (Σ 94% PF) |
| 4[b] | 87 mg | 510-550 | [BMIM][BF$_4$] | 59.9 mg | 14.7 mg | 0.25 (Σ 79% PF) |
|   | 60 mg | 250-380 |                |         | 21.9 mg | 0.06 (Σ 91% PF) |
|   | 55 mg | 250-270 |                |         | 33.5 mg | 0.03 (Σ 94% PF) |
|   | 48 mg | 220-240 |                |         | 35.3 mg | 0.02 (Σ 95% PF) |
| 5[c] | 3.2 mg | 610-640 CO$_2$ (10) | [BMIM][BARF] | 20.2 mg | 20.6 mg | 0.86 (Σ 2.2% PF) |
|   |        | 620-630 educt (1)    |              |         |         |                  |

TABLE 2-continued

Results of continuous experiments (batch experiments as a comparison).

| No | m (12)[a] | CO$_2$-flow rate/µl min$^{-1}$ | IL | m (cat) | m (extract) | product/educt |
|---|---|---|---|---|---|---|
| | 4.6 mg | 290-430 CO$_2$ (10) | | | 36.8 mg | 2.01 (Σ 6.4% PF) |
| | | 280-400 educt (1) | | | | |
| | 4.9 mg | 420-460 CO$_2$ (10) | | | 26.2 mg | 5.40 (Σ 10% PF) |
| | | 460-460 educt (1) | | | | |
| 6[d] | 3.7 mg | 0-5000 CO$_2$ (5) | [BMIM][PF$_6$] | 23.1 mg | first runnings | |
| | | 0-5000 educt (1) | | | | |
| | 2.8 mg | 0-5000 CO$_2$ (5) | | | first runnings | |
| | | 0-5000 educt (1) | | | | |
| | 27.1 mg | 0-6000 CO$_2$ (5) | | | 13.1 mg | 0.64 (Σ 39% PF) |
| | | 0-6000 educt (1) | | | | |
| | 6.9 mg | 280-440 CO$_2$ (5) | | | 0.5 mg | 2.67 (Σ 76% PF) |
| | | 290-440 educt (1) | | | | |
| | 10.1 mg | 410-490 CO$_2$ (5) | | | 1.5 mg | 3.59 (Σ 78% PF) |
| | | 440-480 educt (1) | | | | |
| | 2.0 mg | 310-470 CO$_2$ (5) | | | first runnings | |
| | | 320-480 educt (1) | | | | |
| | 8.3 mg | 260-380 CO$_2$ (5) | | | 1.8 mg | 2.77 (Σ 86% PF) |
| | | 220-370 educt (1) | | | | |
| | 15.2 mg | 290-370 CO$_2$ (5) | | | 1.3 mg | 1.93 (Σ 90% PF) |
| | | 300-350 educt (2) | | | | |
| | 19.6 mg | 280-340 CO$_2$ (5) | | | 4.5 mg | 1.14 (Σ 91% PF) |
| | | 280-320 educt (2) | | | | |
| | 20.7 mg | 280-350 CO$_2$ (5) | | | 5.3 mg | 0.73 (Σ 92% PF) |
| | | 280-360 educt (2) | | | | |
| | 7.2 mg | 340-510 CO$_2$ (5) | | | first runnings | |
| | | 340-510 educt (2) | | | | |
| | 35.2 mg | 360-450 CO$_2$ (5) | | | 14.6 mg | 0.32 (Σ 92% PF) |
| | | 370-440 educt (2) | | | | |
| 7 | 7.5 mg | 200-1000 CO$_2$ (5) | [BMIM][PF$_6$] | 21.0 mg | first runnings | 0.28 |
| | | 200-1000 educt (1) | | | | |
| | 1.5 mg | 0-300 CO$_2$ (5) | | | n.b. | |
| | | 0-300 educt (1) | | | | |
| | 4.6 mg | 400-1800 CO$_2$ (5) | | | n.b. | 1.65 (Σ 24% PF) |
| | | 400-1800 educt (1) | | | | |
| | 11.3 mg | 270-440 CO$_2$ (5) | | | 2.2 mg | 4.54 (Σ 35% PF) |
| | | 270-440 educt (1) | | | | |
| | 16.2 mg | 380-530 CO$_2$ (5) | | | 10.3 mg | 3.48 (Σ 65% PF) |
| | | 380-330 educt (1) | | | | |
| | 13.2 mg | 480-515 CO$_2$ (5) | | | n.d. | 2.11 (Σ 78% PF) |
| | | 480-515 educt (1) | | | | |

Constants: p = 400 bar, T (reactor) = 70° C.,

[a]values were calculated according to the above remarks.

[b]The Nitroveyda catalyst has poor solubility in [BMIM][BF4] -> formation of a suspension; the undissolved part was removed by centrifuging and the metal value of the solution was determined: Ru content = 0.05% -> max. catalyst charge in a given amount of IL = 12 mg

[c]The difference in density between IL and supercritical phase is only very slight, leading to turbulence of the IL in the supercritical phase and hence the discharge -> U$_{max}$ = 500 U/min.

We Claim:
1. A reaction system for carrying out catalytic reactions comprising an ionic liquid, an olefin metathesis catalyst, compressed carbon dioxide and a solid or liquid substrate which can be cyclised by olefin metathesis.
2. A process for preparing cyclic compounds by olefin metathesis, wherein a solid or liquid substrate is reacted in the presence of an olefin metathesis catalyst and a reaction system comprising an ionic liquid and compressed carbon dioxide.
3. Process according to claim 2, wherein a five-fold coordinated ruthenium complex with two anionic ligands, two neutral ligands and one carbene ligand is used as catalyst, wherein the neutral ligands may optionally be linked to the carbene ligand independently of one another.
4. Process according to claim 2, wherein a catalyst of formula A is used;

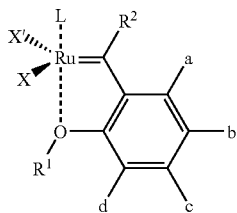

wherein
X and X' denote anionic ligands;
L denotes a neutral ligand;
a, b, c, d independently of one another denote H, halogen, $NO_2$, $C_{1-6}$-alkyl, $CO-R^{a-d}$, $SO_2-R^{a-d}$, $PO(R^{a-d})_2$, $C_{1-6}$-alkoxy or aryl, while aryl may optionally be substituted by a group selected from among $C_{1-6}$-alkyl and $C_{1-6}$-alkoxy;
$R^{a-d}$ denotes $C_{1-8}$-alkyl, $C_{3-6}$-cycloalkyl or aryl, optionally substituted by a group selected from among F, Cl, Br, I, $C_{1-6}$-alkyl, $C_{1-6}$-alkoxy, $NO_2$, CN, $CF_3$, $OCF_3$ or $C_{1-6}$-alkoxycarbonyl;
$R^1$ denotes $C_{1-6}$-alkyl, $C_{1-6}$-haloalkyl, $C_{3-6}$-cycloalkyl, $C_{7-18}$-aralkyl or a group of formula A1, wherein the asterisk indicates the point of attachment to the molecule and

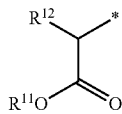

$R^{11}$ denotes $C_{1-6}$-alkyl, $C_{3-6}$-cycloalkyl, $C_{7-18}$-aralkyl, or aryl;
$R^{12}$ denotes H, $C_{1-6}$-alkyl, $C_{3-6}$-cycloalkyl, $C_{7-18}$-aralkyl, or aryl;
$R^2$ denotes H, $C_{1-6}$-alkyl, $C_{2-6}$-alkenyl, $C_{2-6}$-alkynyl or aryl.
5. A process according to claim 2, wherein the ionic liquid corresponds to a salt of formula $[A]_n^+[Y]^{n-}$ where $[A]_n^+$ is the cation, $[Y]^{n-}$ is the anion, and n=1 or 2, which has a melting point below the reaction temperature.
6. A process according to claim 5, wherein the anion $[Y]^{n-}$ is selected from among tetrafluoroborate ($[BF_4]^-$), tetrachloroborate ($[BCl_4]^-$), hexafluorophosphate ($[PF_6]^-$), hexafluoroantimonate ($[SbF_6]^-$), hexafluoroarsenate ($[AsF_6]^-$), tetrachloroaluminate ($[AlCl_4]^-$), trichlorozincate ($[(ZnCl_3]^-$), dichlorocuprate ($[CuCl_2]^-$), sulphate ($[SO_4]^{2-}$), carbonate ($[CO_3]^{2-}$), fluorosulphonate, $[R'-COO]^-$, $[R'-SO_3]^-$, $[R'-SO_4]^-$, [tetrakis-(3,5-bis(trifluoromethyl)-phenyl)borate] ($[BARF]^-$) and $[(R'-SO_2)_2N]^-$, where R' is a straight-chain or branched aliphatic or alicyclic alkyl containing 1 to 12 carbon atoms or a $C_5-C_{18}$-aryl, $C_5-C_{18}$-aryl-$C_1-C_6$-alkyl or $C_1-C_6$-alkyl-$C_5-C_{18}$-aryl group which may be substituted by halogen atoms.
7. A process according to claim 5, wherein the cation $[A]^+$ is selected from among
quaternary ammonium cations of general formula $[NR^1R^2R^3R^4]^+$,
phosphonium cations of general formula $[PR^1R^2R^3R^4]^+$,
imidazolium cations of general formula

wherein the imidazole nucleus may be substituted by at least one group which is selected from $C_1-C_6$-alkyl, $C_1-C_6$-alkoxy, $C_1-C_6$-aminoalkyl, $C_5-C_{12}$-aryl or $C_5-C_{12}$-aryl-$C_1-C_6$-alkyl groups,
pyridinium cations of general formula

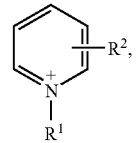

wherein the pyridine nucleus may be substituted by at least one group which is selected from $C_1-C_6$-alkyl, $C_1-C_6$-alkoxy, $C_1-C_6$-aminoalkyl, $C_5-C_{12}$-aryl or $C_5-C_{12}$-aryl-$C_1-C_6$-alkyl groups,
pyrazolium cations of general formula

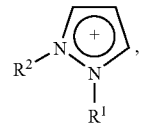

wherein the pyrazole nucleus may be substituted by at least one group which is selected from $C_1-C_6$-alkyl, $C_1-C_6$-alkoxy, $C_1-C_6$-aminoalkyl, $C_5-C_{12}$-aryl or $C_5-C_{12}$-aryl-$C_1-C_6$-alkyl groups and
triazolium cations of general formula

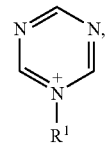

wherein the triazole nucleus may be substituted by at least one group which is selected from $C_1-C_6$-alkyl, $C_1-C_6$-alkoxy, $C_1-C_6$-aminoalkyl, $C_5-C_{12}$-aryl or $C_5-C_{12}$-aryl-$C_1-C_6$-alkyl groups, wherein the groups $R^2$, $R^3$, $R^4$ are selected independently of one another from among hydrogen;

straight-chain or branched, saturated or unsaturated, aliphatic or alicyclic alkyl groups with 1-20 carbon atoms;

heteroaryl or heteroaryl-$C_1$-$C_6$-alkyl groups, with 3 to 8 carbon atoms in the heteroaryl group and at least one heteroatom, selected from N, O and S, which may be substituted by at least one group selected from $C_1$-$C_6$-alkyl groups and/or halogen atoms;

aryl or aryl-$C_1$-$C_6$-alkyl groups, with 5 to 12 carbon atoms in the aryl group which may optionally be substituted by at least one $C_1$-$C_6$-alkyl group and/or one halogen atom; and the group $R^1$ denotes:

straight-chain or branched, saturated or unsaturated, aliphatic or alicyclic alkyl groups with 1-20 carbon atoms;

heteroaryl or heteroaryl-$C_1$-$C_6$-alkyl groups, with 3 to 8 carbon atoms in the heteroaryl group and at least one heteroatom, selected from N, O and S, which may be substituted by at least one group selected from $C_1$-$C_6$-alkyl groups and/or halogen atoms;

aryl or aryl-$C_1$-$C_6$-alkyl groups, with 5 to 12 carbon atoms in the aryl group which may optionally be substituted by at least one $C_1$-$C_6$-alkyl group and/or one halogen atom.

8. A process according to claim 2, wherein the compressed carbon dioxide is present in liquid, gaseous or supercritical form.

9. A process according to claim 2, wherein the substrate is a functionalised or non-functionalised diolefin which is in liquid or solid form at ambient temperature and normal pressure and can be cyclised by olefin metathesis.

10. A process according to claim 2, wherein the substrate and the product have at least partial solubility in the compressed carbon dioxide under reaction conditions.

11. A process according to claim 2, wherein the catalyst is soluble in the ionic liquid and has substantially better solubility in the ionic liquid than in the compressed carbon dioxide phase.

12. A process of carrying out a catalytic reaction in a system comprising an ionic liquid, an olefin metathesis catalyst, compressed carbon dioxide and a solid or liquid substrate which can be cyclised by olefin metathesis.

13. A process according to claim 12, wherein the process is carried out as a continuous operation.

14. A process according to claim 12, wherein the process is carried out as a batch operation and comprises in situ lowering of the pressure of the compressed carbon dioxide phase and recovery of the olefin metathesis cyclisation product from the ionic liquid.

15. A process according to claim 12, wherein the compressed carbon dioxide carries the reaction product and unreacted substrate out from the reactor.

16. A process according to claim 12, wherein a switchable component regulates the delivery of an uncharged and a substrate-charged $CO_2$ current into the reactor according to a timed program.

17. A process according to claim 12, wherein the catalytic reaction is carried out in a series of connected reactors (reactor cascade), in which the reaction mixture is recycled into the same reactor: a) after some of the product has been separated off and replaced by additional substrate and/or b) is used as substrate in subsequent reactors.

18. A process according to claim 12, wherein the reaction temperature is between −50 and 300° C.

19. A process according to claim 12, wherein the overall pressure is between 10 and 1000 bar.

20. A process according to claim 12, wherein the reaction temperature and the overall pressure are selected so that the density of the $CO_2$ phase is between 0.2 and 1.2 g ml$^{-1}$.

* * * * *